United States Patent
Naya et al.

(10) Patent No.: US 9,140,652 B2
(45) Date of Patent: Sep. 22, 2015

(54) LIGHT MEASUREMENT METHOD AND MEASUREMENT APPARATUS USING AN OPTICAL FIELD ENHANCEMENT DEVICE

(71) Applicant: FUJIFILM Corporation, Tokyo (JP)

(72) Inventors: Masayuki Naya, Ashigarakami-gun (JP); Shinya Hakuta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 128 days.

(21) Appl. No.: 13/785,608

(22) Filed: Mar. 5, 2013

(65) Prior Publication Data

US 2013/0182248 A1   Jul. 18, 2013

Related U.S. Application Data

(63) Continuation of application No. PCT/JP2011/004966, filed on Sep. 5, 2011.

(30) Foreign Application Priority Data

Sep. 17, 2010   (JP) .................................. 2010-208984

(51) Int. Cl.
  *G01N 21/65*   (2006.01)
  *G01N 21/64*   (2006.01)
  *G01N 21/63*   (2006.01)

(52) U.S. Cl.
  CPC ............... *G01N 21/65* (2013.01); *G01N 21/63* (2013.01); *G01N 21/64* (2013.01); *G01N 21/648* (2013.01); *G01N 21/658* (2013.01)

(58) Field of Classification Search
  CPC .. G01N 21/658; G01N 21/648; G01N 21/554
  USPC .................................. 356/301, 317–318, 417
  See application file for complete search history.

(56) References Cited

U.S. PATENT DOCUMENTS

| 4,190,321 A | 2/1980 | Dorer et al. |
| 4,252,843 A | 2/1981 | Dorer et al. |

(Continued)

FOREIGN PATENT DOCUMENTS

| CN | 1918467 A | 2/2007 |
| JP | 61-48124 A | 3/1986 |

(Continued)

OTHER PUBLICATIONS

Towata et al., "Fabrication of silver nanoparticles deposited on boehmite sol for surface enhanced Raman scattering", Feb. 18, 2011, Elsevier, Applied Surface Science 257, pp. 6010-6015.*

(Continued)

*Primary Examiner* — Kara E Geisel
(74) *Attorney, Agent, or Firm* — Birch, Stewart, Kolasch & Birch, LLP (57) ABSTRACT

Performing a measurement using an optical field enhancement device which includes a transparent substrate having a transparent fine uneven structure on a surface and a metal film formed on a surface of the fine uneven structure on the surface of the substrate, in which a subject is placed on the metal film of the optical field enhancement device, then excitation light is projected onto an area of the optical field enhancement device on which the subject is placed, and light generated by the projection of the excitation light is detected from a back surface side of the transparent substrate.

9 Claims, 5 Drawing Sheets

(56) References Cited

U.S. PATENT DOCUMENTS

| | | | |
|---|---|---|---|
| 5,455,178 A | 10/1995 | Fattinger | |
| 5,693,152 A | 12/1997 | Carron | |
| 6,406,777 B1 | 6/2002 | Boss et al. | |
| 6,776,962 B1 * | 8/2004 | Boss et al. | 422/82.11 |
| 7,397,559 B1 * | 7/2008 | Bratkovski | 356/301 |
| 2005/0105085 A1 | 5/2005 | Naya | |
| 2006/0119853 A1 | 6/2006 | Baumberg et al. | |
| 2008/0007732 A1 * | 1/2008 | Ja | 356/445 |
| 2008/0037022 A1 | 2/2008 | Nishikawa et al. | |
| 2008/0310026 A1 | 12/2008 | Nakayama et al. | |
| 2009/0273779 A1 | 11/2009 | Baumberg et al. | |
| 2010/0171949 A1 | 7/2010 | Mazur et al. | |

FOREIGN PATENT DOCUMENTS

| | | | |
|---|---|---|---|
| JP | 5-346398 A | 12/1993 | |
| JP | 9-202649 A | 8/1997 | |
| JP | 2005-172569 A | 6/2005 | |
| JP | 2006-514286 A | 4/2006 | |
| JP | 2006-145230 A | 6/2006 | |
| JP | 2008-8631 A | 1/2008 | |
| JP | 2008-519254 A | 6/2008 | |
| JP | 2008-233880 A | 10/2008 | |
| JP | 2008-286778 A | 11/2008 | |
| JP | 4347801 B2 | 10/2009 | |
| JP | 2010-66704 A | 3/2010 | |
| JP | 2010-96645 A | 4/2010 | |
| JP | 2010-203900 A | 9/2010 | |
| WO | WO 2005/078415 A1 | 8/2005 | |
| WO | WO 2008/091858 * | 7/2008 | G01N 21/65 |

OTHER PUBLICATIONS

Japanese Office Action and English translation thereof, dated Feb. 25, 2014, for Japanese Application No. 2010-208984.

Ghadarghadr, S. et al., "Plasmonic array nanoantennas on layered substrates: modeling and radiation characteristics," Optics Express, vol. 17, No. 21, pp. 18556-18570, 2009.

Chinese Office Action Issued Oct. 10, 2014 for related Chinese Application No. 201180044475.5 with an English translation.

Extended European Search Report dated Oct. 31, 2014 for related Application No. 11 82 4737.

Jung-Yen Yang et al. "Detection of *Staphylococcus aureus* Using Hydrothermally Roughened Substrates", 2009 IEEE International Conference on Nano/Molecular Medicine and Engineering—Oct. 18-21, 2009—pp. 210-214.

Chinese Office Action issued May 22, 2015 in corresponding Chinese Application No. 201180044475.5 with an English translation.

* cited by examiner

LIGHT MEASUREMENT METHOD AND MEASUREMENT APPARATUS USING AN OPTICAL FIELD ENHANCEMENT DEVICE

CROSS-REFERENCE TO RELATED APPLICATIONS

This application is a Continuation of PCT International Application No. PCT/JP2011/004966 filed on Sep. 5, 2011, which claims the benefit to Patent Application No. 2010-208984 filed in Japan on Sep. 17, 2010. The entire contents of all of the above applications are hereby expressly incorporated by reference.

TECHNICAL FIELD

The present invention relates to a measurement method and a measurement apparatus for measuring detection light enhanced by the use of an optical field enhancement device having a fine uneven metal structure capable of inducing localized plasmon.

BACKGROUND ART

Electric-field enhancement devices, such as sensor devices, Raman spectroscopy devices, and the like, that utilize an electric-field enhancement effect of a phenomenon of localized plasmon resonance on a metal surface are known. The Raman spectroscopy is a method for obtaining a Raman scattered light spectrum (Raman spectrum) by separating scattered light obtained by projecting single wavelength light onto a substance, and it is used for identifying a substance or the like.

The Raman spectroscopy includes a method called surface-enhanced Raman spectroscopy (SERS) that utilizes an optical field enhanced by localized plasmon resonance in order to enhance weak Raman scattered light as described, for example, in S. Ghadarghadr et al., "Plasmonic array nanoantennas on layered substrates: modeling and radiation characteristics", Optics Express, Vol. 17, No. 21, pp. 18556-18570, 2009. This makes use of the principle that if light is projected onto a metal body, in particular, onto a metal body having a nano-order uneven pattern on a surface with a substance being in contact with the surface, optical field enhancement occurs due to localized plasmon resonance and the intensity of Raman scattered light of the sample in contact with the surface of the metal body is enhanced. The surface-enhanced Raman spectroscopy may be implemented by using a substrate having an uneven metal structure on a surface as a carrier (substrate) for carrying a subject.

As for the substrate having a fine uneven metal structure on a surface, a substrate manufactured by forming an uneven pattern on a surface of a Si substrate and forming a metal film on the surface of the uneven pattern is mainly used as described, for example, in PCT Japanese Publication No. 2006-514286, Japanese Patent No. 4347801, and Japanese Unexamined Patent Publication No. 2006-145230.

Further, a substrate produced by anodizing a surface of an Al substrate to turn a portion into a metal oxide ($Al_2O_3$) layer and filling a metal in a plurality of fine pores spontaneously formed in the metal oxide layer during the anodizing process and opens at the surface of the metal oxide layer is also proposed as described, for example, in Japanese Unexamined Patent Publication No. 2005-172569.

DISCLOSURE OF THE INVENTION

Conventional optical field enhancement substrates disclosed in PCT Japanese Publication No. 2006-514286, Japanese Patent No. 4347801, and Japanese Unexamined Patent Publication Nos. 2006-145230 and 2005-172569 are configured such that a fine uneven structure is formed on a surface of an opaque substrate, such as Si or Al, and a metal film is formed on the surface of the fine uneven structure or a metal is embedded in the depressions. Japanese Unexamined Patent Publication No. 2005-172569 describes an example case in which a transparent substrate, such as a glass substrate, is used, but the fine uneven structure itself is made of an opaque material, such as silicon or germanium.

Conventional Raman spectroscopy apparatuses are configured such that Raman scattered light is detected from the front surface side of a sample. In the case where a sample having a size in the order of micrometers or greater is used as the subject, however, the sample itself acts as a blocking body against the Raman scattered light, whereby it has been difficult to receive weak Raman scattered light with a high signal-to-noise ratio.

The present invention has been developed in view of the circumstances described above, and it is an object of the present invention to provide a measurement method and a measurement apparatus capable of performing a measurement with an improved signal-to-noise ratio in measurement methods and measurement apparatuses in which an optical field enhancement effect of localized plasmon is used to enhance and detect weak light.

A measurement method of the present invention is a method using an optical field enhancement device which includes a transparent substrate having a transparent fine uneven structure on a surface and a metal film formed on a surface of the fine uneven structure on the surface of the substrate, the method comprising the steps of:

placing a subject on the metal film of the optical field enhancement device;

projecting excitation light onto an area of the optical field enhancement device on which the subject is placed; and detecting light generated by the projection of the excitation light from a back surface side of the transparent substrate.

When projecting excitation light onto an area of the optical field enhancement device where the subject is placed, the excitation light may be projected from any direction with respect to the device and, for example, the excitation light may be projected from a front surface side of the metal film or from a back surface side of the transparent substrate.

Preferably, the excitation is projected from the back surface side of the transparent substrate.

Any of Raman scattered light, fluorescence, and a high-order harmonic may be detected as the light generate by the projection of the excitation light.

Further, Rayleigh scattered light, Mie scattered light, or the like generated by the projection of the excitation light may also be detected.

A measurement apparatus of the present invention is an apparatus, including:

an optical field enhancement device which includes a transparent substrate having a transparent fine uneven structure on a surface and a metal film formed on a surface of the fine uneven structure on the surface of the substrate, wherein a subject is placed on a front surface side of the device on which the metal film is formed;

an excitation light projection section for projecting excitation light onto an area of the optical field enhancement device on which the subject is placed; and a light detection section disposed on a back surface side of the optical field enhancement device and configured to detect light generated by the projection of the excitation light from a back surface side of the transparent substrate.

Preferably, the excitation projection section is disposed on the back surface side of the optical field enhancement device and configured to project the excitation light from the back surface side of the transparent substrate.

The metal film of the optical field enhancement device used in the measurement method and measurement apparatus of the present invention is formed on the surface of the fine uneven structure and has a fine uneven structure on the surface according to the transparent fine uneven structure. The fine uneven structure on the surface of the metal film may be anything as long as it is capable of generating localized plasmon by receiving light. Generally, the fine uneven structure capable of generating localized plasmon is an uneven structure having an average size and an average pitch of protrusions and depressions constituting the uneven structure smaller than the wavelength of the light.

Preferably, the average pitch of the protrusions and depressions and the distance (depth) between the top of a protrusion and the bottom of a depression are not greater than 200 nm.

The average pitch of the protrusions and depressions is obtained by imaging the surface of the fine uneven structure with a SEM (Scanning Electron Microscope), then digitizing the image through image processing, and performing a statistical procedure.

The average depth of the protrusions and depressions is obtained by measuring the surface shape with an AFM (Atom Force Microscope) and performing a statistical procedure.

The term "transparent" as used herein refers to having a transmittance of 50% or greater for the light projected onto the fine uneven structure and light generated from the subject by the projected light. Preferably, the transmittance for these light beams is not less than 75% and more preferably, not less than 90%.

In the optical field enhancement device described above, the transparent substrate may be formed of a transparent substrate body and a fine uneven structure layer provided on a surface of the transparent substrate body, wherein the layer is made of a material different from that of the transparent substrate body and constitutes the fine uneven structure.

In particular, the fine uneven structure layer may preferably be made of boehmite.

The metal film may be any film made of a metal that generates localized plasmon by receiving the light described above, but at least one type of metal selected from the group consisting of Au, Ag, Cu, Al, Pt, and alloys based on these metals is preferable. Among them, Au and Ag are particularly preferable.

Preferably, the metal film has a film thickness of 10 to 100 nm.

The measurement apparatus may include a transparent second fine uneven structure acting as an antireflection film on the back surface of the transparent substrate of optical field enhancement device.

Here, it is preferable that the second fine uneven structure is formed of a fine uneven structure layer made of boehmite.

The optical field enhancement device described above may be formed into a sample cell having a liquid sample holding member for holding a liquid sample on the metal film of the transparent substrate.

Further, the optical field enhancement device described above may be a flow cell type sample cell, wherein the liquid sample holding member has an inlet section and an outlet section for a liquid.

The measurement method and measurement apparatus of the present invention use an optical field enhancement device which includes a transparent substrate having a transparent fine uneven structure on a surface and a metal film formed on a surface of the fine uneven structure on the surface of the substrate and configured to detect light (detection light) generated by the projection of excitation light onto an area of the device on which a subject is placed from a back surface side of the transparent substrate.

The optical field enhancement device includes a transparent uneven structure on which a metal film is provided and, thus, the metal film itself is formed in an uneven pattern. This allows localized plasmon to be effectively induced on the surface of the metal film by projecting excitation light onto the metal film and an optical field enhancement effect of the localized plasmon may be obtained. Further, if a substrate is placed on the optical field enhancement device and light is projected onto an area of the device on which the subject is placed, light generated from the subject is enhanced by the optical field enhancement effect, whereby the light can be detected with high sensitivity.

In the measurement method and apparatus of the present invention, in particular, light (detection light) generated from the subject is detected from the back surface side of the transparent substrate, the light enhanced by the enhanced optical field having a maximum intensity on the surface of the metal film can be detected without being blocked by the subject. Therefore, the light may be measured with a favorable signal-to-noise ratio.

BEST MODE FOR CARRYING OUT THE INVENTION

Hereinafter, embodiments of the measurement method and measurement apparatus of the present invention will be described with reference to the accompanying drawings. Each component in the drawings is not necessarily drawn to scale for ease of visual recognition.

First Embodiment

Figure 1:
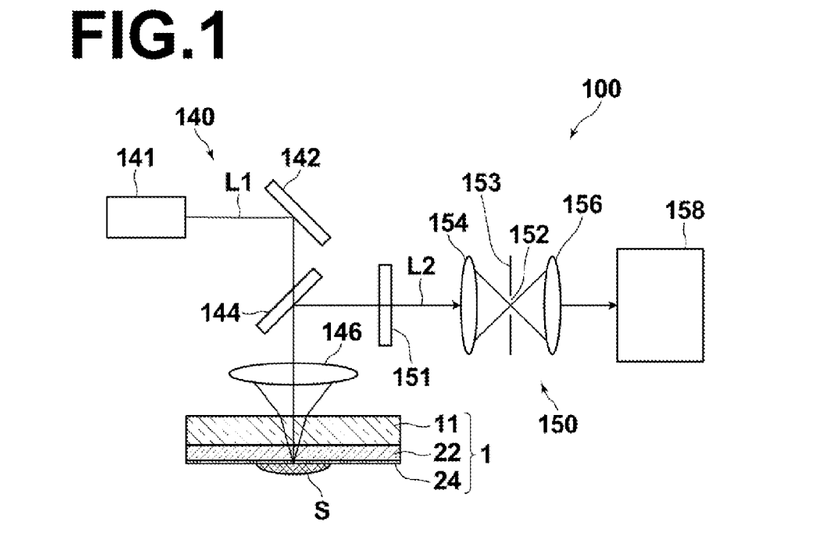
FIG. 1 is a schematic diagram of a Raman spectroscopy apparatus according to a first embodiment of the measurement apparatus of the present invention, illustrating the configuration thereof.

As a first embodiment of the measurement method and measurement apparatus of the present invention, a Raman spectroscopy method and a Raman spectroscopy apparatus 100 will be described. FIG. 1 is a schematic diagram of the Raman spectroscopy apparatus 100 according to the first embodiment, illustrating the configuration thereof.

As illustrated in FIG. 1, the Raman spectroscopy apparatus 100 includes an optical field enhancement substrate 1 for supporting a subject S, an excitation light projection section 140 for projecting excitation light L1 onto an area of the optical field enhancement substrate 1 on which the subject S is placed from a back surface side of the substrate 1, and a light detection section 150 for detecting Raman scattered light L2 emitted from the subject S and enhanced by the action of the optical field enhancement substrate 1 from the back surface side of the substrate 1.

Figure 2A:
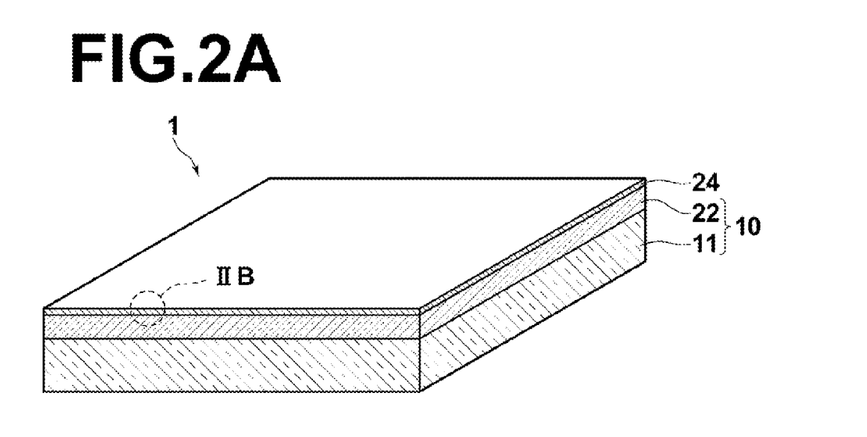
FIG. 2A is a perspective view of an optical field enhancement substrate provided in the Raman spectroscopy apparatus shown in FIG. 1.

The optical field enhancement substrate 1 will be described first. FIG. 2A is a perspective view of the optical field enhancement substrate 1 and FIG. 2B is an enlarged view of a portion IIB of a side face of the optical field enhancement substrate 1 shown in FIG. 2A.

Figure 2B:
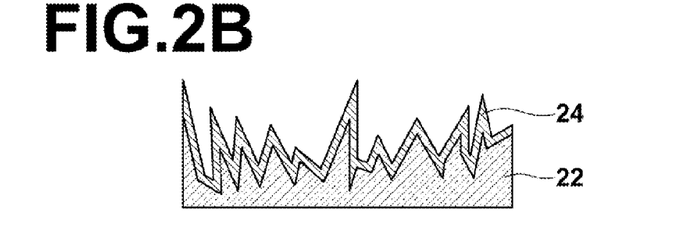
FIG. 2B is an enlarged view of a portion IIB of a side face of the optical field enhancement substrate shown in FIG. 2A.

As illustrated in FIGS. 2A, 2B, the optical field enhancement substrate 1 includes a transparent substrate 10 having a fine uneven structure 22 on a surface and a metal film 24 formed on a surface of the fine uneven structure 22. The metal film 24 is formed along the fine uneven structure 22 such that a fine metal uneven structure is formed. Thus, the optical field enhancement substrate 1 includes a fine uneven metal structure on a surface and may function as an optical field enhancement device capable of obtaining an optical field enhancement effect of localized plasmon resonance.

The optical field enhancement substrate 1 is configured such that localized plasmon resonance is induced by light (excitation light) projected onto the fine uneven structure 22 on which the metal film 24 is formed (fine uneven metal structure), and enhanced optical field is created on the surface of the metal film 24 by the localized plasmon resonance.

The fine uneven structure 22 is an uneven structure of a size that causes the average size and pitch of protrusions of uneven pattern on the fine metal structure provided by forming the metal film 24 on the fine uneven structure 22 to become smaller than the wavelength of the excitation light, but the fine uneven structure 22 may be anything as long as it is capable of generating localized plasmon. In particular, it is preferable that the fine uneven structure 22 has an average depth of not greater than 200 nm from the top of a protrusion to the bottom of an adjacent depression and an average pitch of not greater than 200 nm between the tops of the most adjacent protrusions across a depression.

In the present embodiment, the transparent substrate 10 is formed of a transparent substrate body 11 made of glass or the like and a boehmite layer made of a material different from that of the body 11 and constitutes the fine uneven structure 22 (hereinafter, referred to as "boehmite layer 22" or "fine uneven structure layer 22").

The metal film 24 may be any film made of a metal that generates localized plasmon by receiving the light described above, but at least one type of metal selected from the group consisting of Au, Ag, Cu, Al, Pt, and alloys based on these metals is preferable. Among them, Au and Ag are particularly preferable.

There is not any specific restriction on the thickness of the metal film 24 as long as it is capable of maintaining an uneven pattern shape capable of causing localized plasmon by receiving excitation light as the fine uneven metal structure when formed on the surface of the fine uneven structure layer 22, and a thickness of 10 to 100 nm is preferable.

The excitation light projection section 140 includes a semiconductor laser 141 that emits the excitation light L1, a mirror 142 that reflects the light L1 emitted from the semiconductor laser 141 toward the substrate 1, a half-mirror 144 that transmits the excitation light L1 reflected from the mirror 142 and reflects light from the substrate 1, which includes Raman scattered light L2 generated from the subject S by receiving the excitation light L1 and enhanced, toward the light detection section 150, and a lens 146 that focuses the excitation light L1 transmitted through the half mirror 144 on an area of the optical field enhancement substrate 1 on which the subject S is placed and collimates light from the side of the subject S.

The light detection section 150 includes a notch filter 151 that absorbs the excitation light L1 included in the light reflected from the half mirror 144 and transmits light other than the excitation light, a pin-hole plate 153 having a pin-hole 152 for removing noise light, a lens 154 that focuses the enhanced Raman scattered light L2 emitted from the subject S and transmitted through the lens 146 and the notch filter 151 on the pin-hole 152, a lens 156 that collimates the Raman scattered light passed through the pin-hole 152, and a spectroscope 158 that detects the enhanced Raman scattered light.

A Raman spectroscopy method for measuring a Raman spectrum of the subject S using the aforementioned Raman spectroscopy apparatus 100 will now be described.

The excitation light L1 is emitted from the semiconductor laser 141 of the light projection section 140, reflected by the mirror 142 toward the substrate 1, transmitted through the half mirror 144, focused by the lens 146, and projected onto the optical field enhancement substrate 1.

The projection of the excitation light L1 onto the optical field enhancement substrate 1 causes localized plasmon resonance to be induced in the fine uneven metal structure, and enhanced optical field is created on the surface of the metal film 24. Raman scattered light L2 emitted from the subject S and enhanced by the enhanced optical field is transmitted through the lens 146, reflected by the half mirror 144 toward the spectroscope 158. Here, the excitation light L1 reflected from the optical field enhancement substrate 1 is reflected by the half mirror 144 toward the spectroscope 158, but it is cut by the notch filter 151. In the mean time, light having a wavelength different from that of the excitation light is passed through the notch filter 151, focused by the lens 154, passed through the pin-hole 152, collimated again by the lens 156, and incident on the spectroscope 158. In a Raman spectroscopy apparatus, Rayleigh scattered light (or Mie scattered light) has the same wavelength as that of the excitation light L1 so that it is cut by the notch filter 151 and never incident on the spectroscope 158. The Raman scattered light L2 is incident on the spectroscope 158 and Raman spectrum measurement is performed.

The Raman spectroscopy apparatus 100 of the present embodiment is configured using the optical field enhancement substrate 1 and Raman enhancement takes place effectively so that highly accurate Raman spectroscopy measurement with high data reliability and reproducibility can be conducted. As the uneven structure on the surface of the optical field enhancement substrate 1 has high in-plane uniformity, reproducible data may be obtained even when the measurement is repeated with respect to the same sample by changing the position where the light is projected. It is, therefore, possible to increase the reliability of data by obtaining a plurality of data with respect to the same sample by changing the position where the light is projected.

Adoption of a configuration in which detection is performed from the back surface side of the optical field enhancement substrate 1, as in the Raman spectroscopy apparatus 100 of the present embodiment, allows the enhanced Raman scattered light that occurs most strongly at the interface between the metal film and subject to be detected from the back surface side of the transparent substrate without being blocked by the subject even when the subject is a large sample like a cell. The present inventors have confirmed that enhanced Raman scattered light can be detected from the back surface side of the transparent substrate without being affected by the metal film (Example to be described later).

The aforementioned embodiment has a configuration in which both the excitation light projection section 140 and light detection section 150 are disposed on the back surface side of the optical field enhancement substrate 1 and excitation light is projected from the back surface side. But a configuration may be adopted in which the excitation light projection section 140 is disposed on a front surface side (surface side on which the subject is placed) of the optical field enhancement substrate 1 and excitation light is projected from the front surface side. Localized plasmon may be induced in a similar fashion on the fine uneven metal structure of the optical field enhancement substrate regardless of whether excitation light is incident from the front surface side or back surface side, and an optical field enhancement effect may be obtained.

Further, in the aforementioned embodiment, the description has been made of a case in which the fine uneven structure layer 22 is made of boehmite, but the layer may be made of a transparent material other than the boehmite. For example, the transparent substrate 10 may also be formed by performing an anodization process on an aluminum substrate to produce an anodized alumina having multiple fine pores in an upper layer of the aluminum substrate, removing the unanodized aluminum portion to obtain an anodized alumina layer as the fine uneven structure layer 22, and fixing the fine uneven structure layer 22 on the transparent substrate body 11 made of glass or the like.

The fine uneven structure is not limited to the structure made of a material different from that of the transparent substrate body and it may be made of the same material as that of the substrate body by processing the surface of the transparent substrate body. For example, a glass substrate having a fine uneven structure on a surface formed through lithography and dry-etching may be used as the transparent substrate.

The fine uneven structure 22 is most preferably made of boehmite as it is formed by an easy method.

Figure 3:
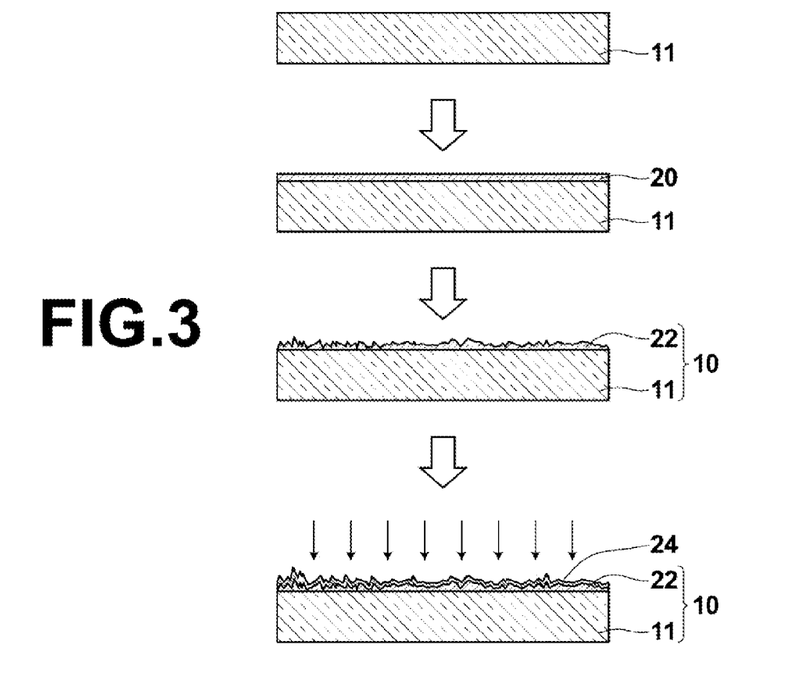
FIG. 3 shows a manufacturing method of an optical field enhancement substrate, illustrating a cross-section of the substrate at each step of the method.

A method of manufacturing the optical field enhancement substrate 1 according to the present embodiment will now be described with reference to FIG. 3. FIG. 3 illustrates a cross-section of the optical field enhancement substrate 1 at each manufacturing step.

A plate-like transparent substrate body 11 is provided. Then, the transparent substrate body 11 is cleaned with pure water. Thereafter, aluminum 20 is formed on the transparent substrate body 11 with a thickness of about several tens of nanometers by sputtering. Then, the transparent substrate body 11 with the aluminum 20 is immersed in boiling pure water and taken out after several minutes (about five minutes). This boil treatment (boehmite treatment) turns the aluminum 20 into the transparent boehmite layer 22 constituting a fine uneven structure. Then, a metal film 24 is formed on the boehmite layer 22. In this way, the optical field enhancement substrate 1 is created.

Figure 4A:
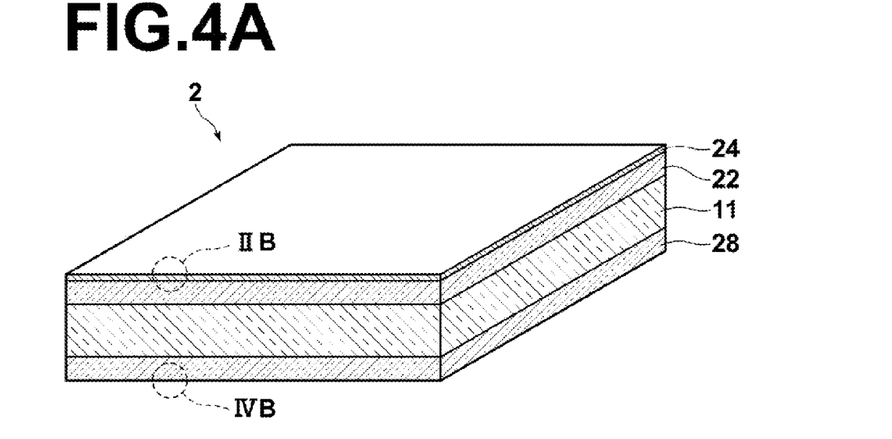
FIG. 4A is a perspective view of a design change example of the optical field enhancement substrate.
Figure 4B:
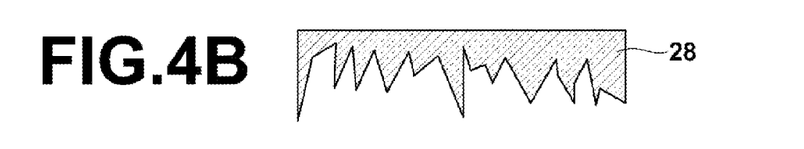
FIG. 4B is an enlarged view of a lower portion IVB of a side face of the optical field enhancement substrate shown in FIG. 4A.

A design change example of the optical field enhancement substrate 1 for the Raman spectroscopy apparatus 100 of the present embodiment will be described. FIG. 4A is a perspective view of an optical field enhancement substrate 2 of a design change example and FIG. 4B is an enlarged view of a lower portion IVB of a side face of the optical field enhancement substrate 2 shown in FIG. 4A.

The optical field enhancement substrate 2 includes a transparent second fine uneven structure layer 28 on the back surface of the optical field enhancement substrate 1 described above.

The second fine uneven structure layer 28 is identical to the first fine uneven structure layer 22 provided on the front surface of the transparent substrate 10 and may be made of a boehmite layer. The fine uneven structure layer 28 provided on the back surface functions as an antireflection film when light is projected.

The optical field enhancement substrate 2 may be obtained by forming aluminum on the back surface of the transparent substrate as well as on the front surface in the method of manufacturing the optical field enhancement substrate 1 of the first embodiment and performing a boil treatment after that. The aluminum on the front and back surfaces of the substrate turns into boehmite through boil treatment in pure water and the optical field enhancement substrate 2 may have similar fine uneven structures 22, 28 on the front and back surfaces respectively.

For a transparent substrate (BK-7, Coring, Eagle 2000) having a boehmite layer formed by sputtering aluminum on the substrate with a thickness of 50 nm and boil treating the boehmite layer for five minutes, the present inventors have confirmed that, when light is inputted from the front surface side of the boehmite layer at right angle with respect to the surface, a reflectance of about 0.1% is achieved. The wavelength where the reflectance becomes minimal can be adjusted, for example, by changing the thickness of aluminum formed first by sputtering and controlling interference.

Second Embodiment

Figure 5:
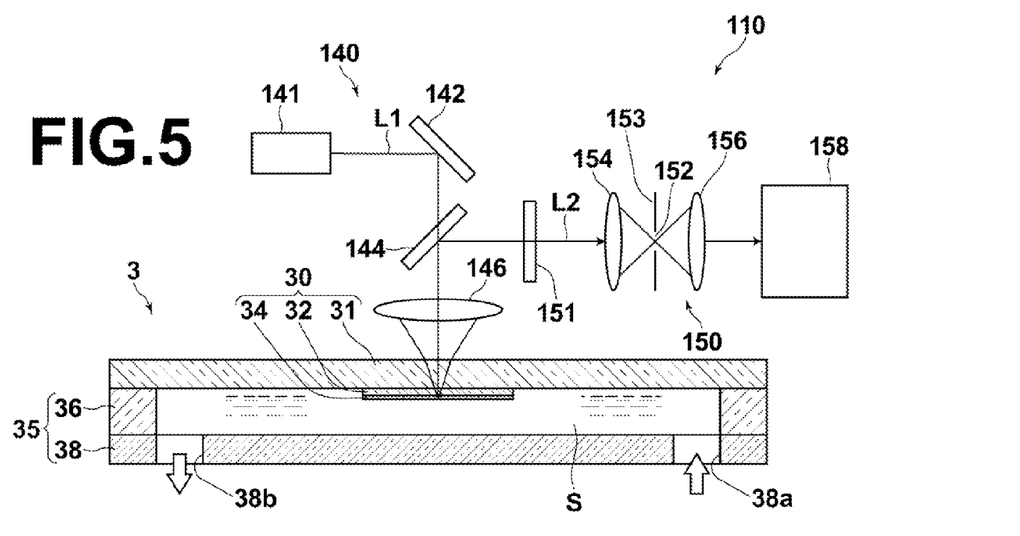
FIG. 5 is a schematic diagram of a Raman spectroscopy apparatus according to a second embodiment of the measurement apparatus of the present invention, illustrating the configuration thereof.

A Raman spectroscopy method and a Raman spectroscopy apparatus 110 according to a second embodiment of the present invention will be described. FIG. 5 is a schematic diagram of the Raman spectroscopy apparatus 110 according to the second embodiment, illustrating the configuration thereof.

As illustrated in FIG. 5, the Raman spectroscopy apparatus 110 differs from the Raman spectroscopy apparatus 100 shown in FIG. 1 in that it includes a flow cell type optical field enhancement sample cell 3 instead of the optical field enhancement substrate 1. Provision of such flow cell type optical field enhancement device allows Raman spectrum to be measured while a liquid sample, as the subject, is flowing down. In FIG. 5, components identical to those used in the first embodiment are given the same reference symbols and will not be elaborated upon further here. The Raman spectroscopy method is also identical to that using the Raman spectroscopy apparatus 100 of the first embodiment.

Figure 6A:
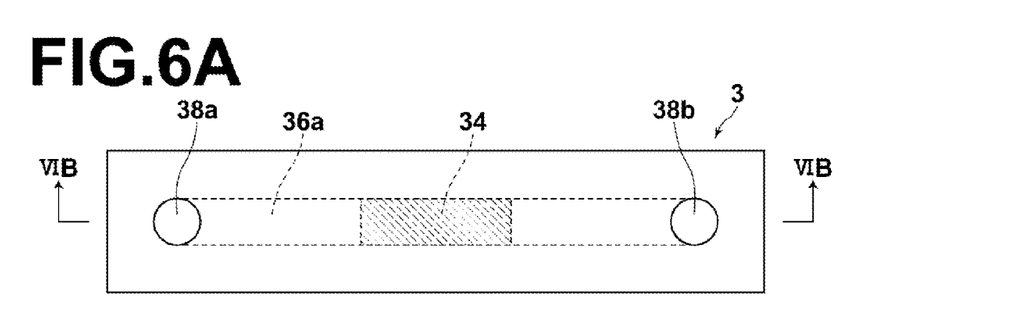
FIG. 6A is a plan view of an optical field enhancement sample cell provided in the Raman spectroscopy apparatus shown in FIG. 5.
Figure 6B:
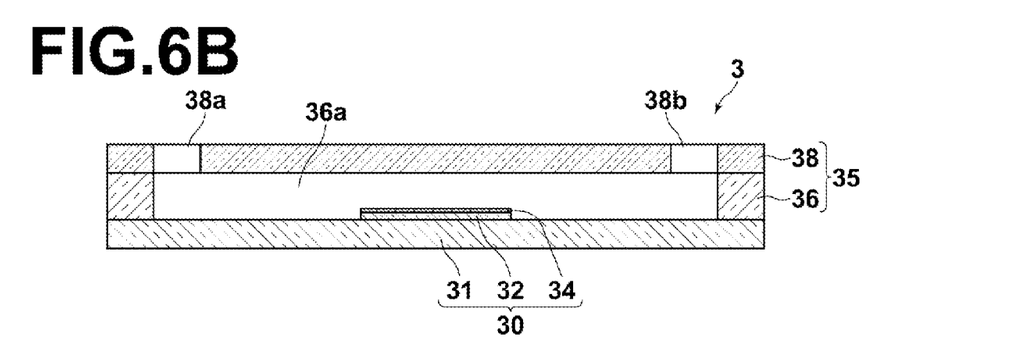
FIG. 6B is a cross-sectional view of the optical field enhancement sample cell shown in FIG. 6A taken along the line VIB-VIB.

The optical field enhancement sample cell 3 of the Raman spectroscopy apparatus 110 will now be described. FIG. 6A is a plan view of the optical field enhancement sample cell 3 and FIG. 6B is a cross-sectional view of the optical field enhancement sample cell 3 taken along the line VIB-VIB in FIG. 6A.

The optical field enhancement sample cell 3 of the present embodiment includes: an optical field enhancement substrate 30 having a transparent substrate body 31, a transparent fine uneven structure 32 provided on the surface of the body, and metal film 34 provided on the fine uneven structure 32; and a liquid sample holding member 35 for holding a liquid sample provided on the metal film 34.

The structure of the optical field enhancement substrate 30 is substantially identical to that of the optical field enhancement substrate 1 of the first embodiment. That is, the fine uneven structure 32 and the metal film 34 are identical to the fine uneven structure 22 and the metal film 24 shown in FIG. 2B, and their constituent materials and forming methods are also identical.

For example, the liquid sample holding member 35 may be formed of a spacer 36 for holding a liquid sample on the metal film 34 and forming a flow path 36a and a transparent upper plate 38, such as a glass plate, having an injection port (inlet) 38a for injecting a liquid sample and a discharge port (outlet) 38b for discharging the liquid sample flowed down the flow path 36a.

The optical field enhancement sample cell 3 of the present embodiment may be obtained by manufacturing the optical field enhancement substrate 30 by a method identical to that of the substrate 1 of the first embodiment and bonding the spacer 36 and the upper plate to the substrate 30.

Note that the spacer 36 and the upper plate 38 may be formed integrally. Alternatively, the spacer 36 may be formed integrally with the transparent substrate body 31.

In the aforementioned embodiment, the description has been made of a case in which an optical field enhancement device of a type of a flow-path-like sample cell (flow cell) having an inlet and an outlet. But it may be configured as an optical field enhancement sample cell only for holding a liquid sample on the metal film instead of a cell capable of flowing in and out a liquid.

Further, a second transparent fine uneven structure layer that functions as an antireflection film may be provided on an area of the back surface of the optical field enhancement substrate 30 corresponding to the area of the metal film 34, as in the optical field enhancement substrate 2 described above.

When measuring Raman scattered light while a liquid sample is flowing down, the transmittance and absorptance of the liquid sample with respect to the Raman scattered light may vary with the movement of the liquid sample, a configuration in which Raman scattered light is detected from the back surface side of the substrate 30, as in the present embodiment, is preferable since the influence of the variations due to the movement of the liquid sample may be reduced in comparison with a case in which the Raman scattered light is detected from the sample side (metal film surface side) as in a conventional method.

Third Embodiment

Figure 7:
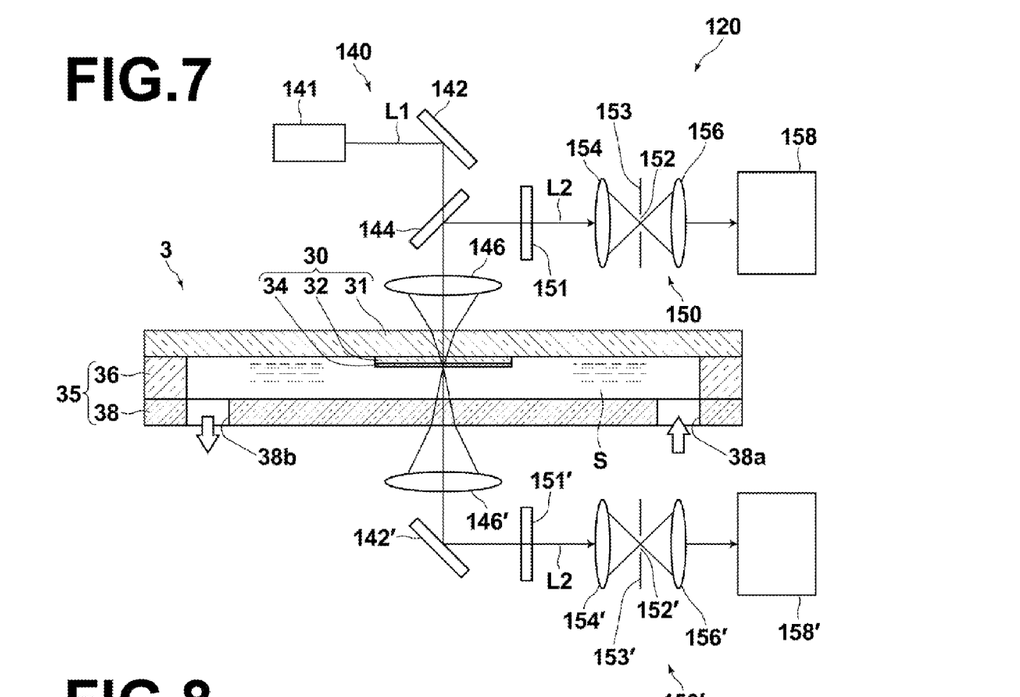
FIG. 7 is a schematic diagram of a Raman spectroscopy apparatus according to a third embodiment of the measurement apparatus of the present invention, illustrating the configuration thereof.

A Raman spectroscopy method and a Raman spectroscopy apparatus 120 according to a third embodiment of the present invention will be described. FIG. 7 is a schematic diagram of the Raman spectroscopy apparatus 120 according to the third embodiment, illustrating the configuration thereof.

As illustrated in FIG. 7, the Raman spectroscopy apparatus 120 further includes a second light detection section 150' in the Raman spectroscopy apparatus 110 of the second embodiment.

The second light detection section 150' includes a condenser lens 146' that condenses light emitted from the subject S, a mirror 142' that reflects the light transmitted through the condenser lens 146' toward a right angle direction, a notch filter 151' that absorbs the excitation light L1 and passes light other than the excitation light L1, a pin-hole plate 153' having a pin-hole 152' for removing noise light, a lens 154' that focuses the enhanced Raman scattered light L2 emitted from the subject S and transmitted through the lens 146' and the notch filter 151' on the pin-hole 152', a lens 156' that collimates the Raman scattered light passed through the pin-hole 152', and a spectroscope 158' that detects the enhanced Raman scattered light.

A Raman spectroscopy method for measuring a Raman spectrum of the subject S using the Raman spectroscopy apparatus of the present embodiment will be described.

Excitation light L1 is emitted from the semiconductor laser 141 of the light projection section 140, reflected by the mirror 142 toward the substrate 30, transmitted through the half mirror 144, focused by the lens 146, and projected onto the metal film 34 in contact with the liquid sample S which is a subject of the optical field enhancement substrate 30.

The projection of the excitation light L1 causes localized plasmon resonance to be induced in the fine uneven metal structure of the optical field enhancement substrate 30, and enhanced optical field is created on the surface of the metal film 34. Raman scattered light L2 emitted from the subject S and enhanced by the enhanced optical field is transmitted through the lens 146 from the back surface side of the substrate 30, reflected by the half mirror 144 toward the spectroscope 158. At the same time, the light L2 is transmitted through the subject S from the front surface side of the metal film 34, further transmitted through the lens 146' and reflected by the mirror 142' toward the spectroscope 158'. Here, the excitation light L1 reflected from the optical field enhancement substrate 30 is reflected by the half mirror 144 toward the spectroscope 158, but it is cut by the notch filter 151. In the mean time, light having a wavelength different from that of the excitation light is transmitted through the notch filter 151, focused by the lens 154, passed through the pin-hole 152, collimated again by the lens 156, and incident on the spectroscope 158. Similarly, the excitation light L1 transmitted through the optical field enhancement substrate 30 is transmitted through the lens 146' and reflected by the mirror 142' toward the spectroscope 158', but it is cut by the notch filter 151'. In the mean time, light having a wavelength different from that of the excitation light is transmitted through the notch filter 151', focused by the lens 154', passed through the pin-hole 152', collimated again by the lens 156', and incident on the spectroscope 158'.

Provision of the light detection sections 150, 150' on the front surface side and back surface side of the transparent substrate of the optical field enhancement device, as in the present embodiment, allows the detection sensitivity to be increased by adding signals obtained by the two spectroscopes 158 and 158' by a not shown data processing section.

The Raman spectroscopy apparatus and method according to each embodiment described above uses the optical field enhancement substrate 1, 2, or 30 which includes a transparent substrate having a transparent uneven structure and a metal film provided on the surface of the uneven structure, in which a subject is placed on the fine uneven metal structure, then excitation light is projected onto the place on which the subject is placed, and light generated from the subject by the projection of the excitation light is detected from the back surface side of the transparent substrate. This allows Raman scattered light (detection light) enhanced by the optical field enhancement effect that occurs most strongly on the surface of the fine uneven metal structure to be detected regardless of the type or size of the subject.

Raman spectroscopy methods and Raman spectroscopy apparatuses have been described as the embodiments of the measurement method and measurement apparatus of the present invention, but the measurement method and measurement apparatus of the present invention may also be applied to a plasmon enhanced fluorescence detection method and a fluorescence detection apparatus. In the fluorescence detection apparatus, the optical field enhancement substrate 1 or 2, or the optical field enhancement sample cell 3 is used, then a subject is placed on the metal film, and excitation light is projected from the subject side or from the transparent substrate side, whereby enhanced fluorescence may be detected from the back surface side of the substrate.

Further, in a measurement method and a measurement apparatus for measuring not only the Raman scattered light or fluorescence but also Rayleigh scattered light, Mie scattered light, or second harmonics generated from a subject that has received excitation light, the optical field enhancement substrate 1 or 2, or the optical field enhancement sample cell 3 is used, then a subject is placed on the metal film, and excitation light is projected from the subject side or from the transparent substrate side, whereby enhanced optical field associated with localized plasmon resonance may be created and enhanced light may be detected.

EXAMPLE

Hereinafter, a specific example of the optical field enhancement substrate 1 provided in the Raman spectroscopy apparatus according to the first embodiment of the present invention, and Raman spectroscopy measurement results using a measuring sample will be described.

[Manufacturing Method of Optical Field Enhancement Substrate]

A glass substrate (BK-7, Corning Eagle 2000) was used as the transparent substrate body 11. Then, the substrate was cleaned by ultrasonic cleaning (45 kHz, three minutes) with pure water. Aluminum 20 was layered on the cleaned glass substrate 11 with a thickness of 50 nm using a sputtering system (CANON ANELVA Corporation). The thickness of the aluminum was measured using a profilometer (TENCOR Corporation) and verified to be 50 nm (±10%). Then, a container containing pure water was placed on a hot plate to boil the pure water. The glass substrate 11 with the aluminum 20 was immersed in the boiling water and taken out after five minutes. Here, it was confirmed that the aluminum turned to transparent about one or two minutes after it was immersed in the boiling water. This boil treatment (boehmite treatment) turned the aluminum 20 to the boehmite layer 22. Finally, Au was deposited on the boehmite layer 22 with a thickness of 40 nm as the metal film 24.

[Raman Scattered Light Measurement]

Using a dye (Rhodamine 6G)-attached measuring sample, as a subject, on the optical field enhancement substrate manufactured in the manner described above, Raman scattered light was measured from the front and back surface sides of the substrate.

(Method of Producing Measuring Sample)

A method of producing the measuring sample will be described with reference to FIG. 8.

An optical field enhancement substrate produced by placing a mask on a peripheral portion of a transparent substrate when the metal film was formed on the transparent fine uneven structure layer by vapor deposition and removing the mask after the deposition in the method of manufacturing the optical field enhancement substrate 1 was used. Thus, the metal film was not formed on the masked area of the measuring sample optical field enhancement substrate.

Figure 8:
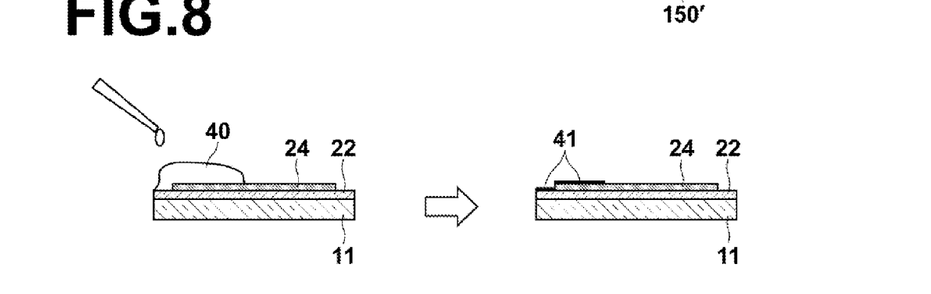
FIG. 8 shows schematic cross-sectional views of a measuring sample in an Example, illustrating the manufacturing steps thereof.

First, a solution (R6G/ethanol: 10 mM) 40 which includes a dye (Rhodamine 6G) was dropped on an area where the gold film 24 was formed and an area where it was not formed, as illustrated in the drawing on the left of FIG. 8.

Then, by drying the droplet, a measuring sample in which the dye 41 was fixed on both of the areas with and without the metal film 24 was obtained, as illustrated in the drawing on the right of FIG. 8.

(Raman Scattered Light Measurement Method)

Figure 9:
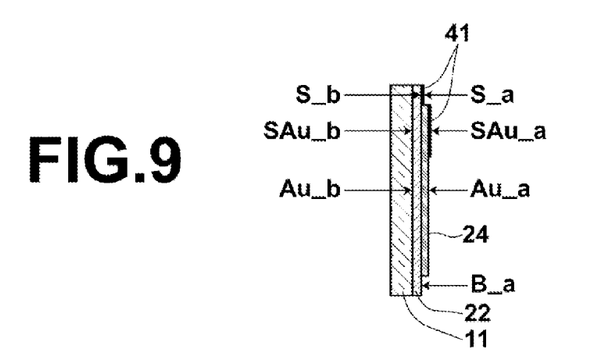
FIG. 9 is a cross-sectional view of the measuring sample, illustrating positions for measuring Raman scattered light.

Excitation light was projected onto seven measuring points of the measuring sample illustrated in FIG. 9, namely, front surface side of boehmite B_a, front surface side of gold film Au_a, back surface side of gold film Au_b, front surface side of the dye on the gold film SAu_a, back surface side of the dye on the gold film SAu_b, front surface side of the dye on the boehmite S_a, and back surface side of the dye on the boehmite S_b, and Raman scattered light was measured.

Raman scattered light was detected using a microscopic Raman spectroscopy apparatus (Raman 5). For example, the measurement of the front surface side of the dye on the metal film is a measurement in which the excitation light was projected from the front surface side of the dye on the metal film and Raman scattered light was detected from the front surface side of the dye on the metal film. As for the excitation light, laser light with a peak wavelength of 785 nm was used and observation was performed with a magnification of 20.

(Measurement Results)

Figure 10:
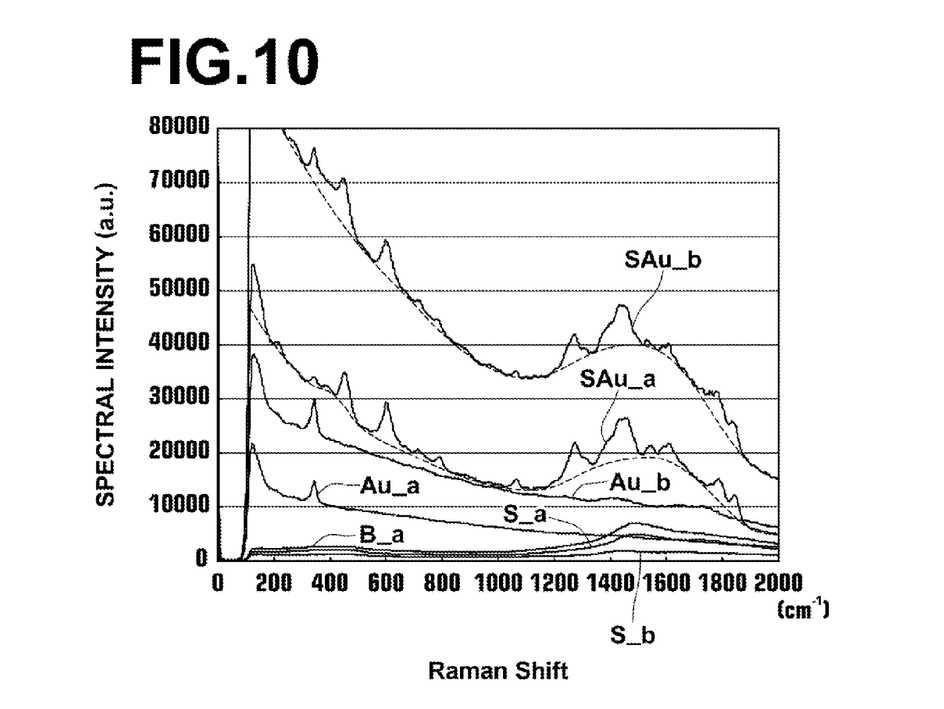
FIG. 10 is a graph illustrating a Raman shift spectrum distribution obtained from the measuring sample.

FIG. 10 is a graph illustrating a Raman shift spectrum distribution from each position detected by the microscopic Raman spectroscopy apparatus.

Virtually no signal of Raman scattered light was detected from the front surface side of boehmite B_a, front surface side of the dye fixed on the boehmite S_a, and back surface side of the dye on the boehmite S_b. As described above, it is known that the signal at a position where the gold film was not provided is very low measured from the front surface side or from the back surface side.

With respect to the position where the dye was fixed on the gold film, high intensity spectrum was obtain in each detection from the front surface side SAu_a and back surface side SAu_b but with a high background. In FIG. 10, portions that can be regarded as backgrounds are indicated by the dashed lines. Signals obtained by subtracting the backgrounds can be pure Raman shift signals. Raman shift signals detected at the corresponding positions between detection from the front surface side and back surface side of the dye on the gold film SAu_a and SAu_b were identical in intensity.

Heretofore, there has been no case in Raman measurement in which a Raman signal is detected from the back surface side of the substrate, and present inventors have found out that a Raman signal can be detected from the back surface side of the substrate through the aforementioned Raman measurement using the optical field enhancement device of the present invention.

From the measurement results, the present inventors assume that an optical field enhanced by localized plasmon created by the light projected onto the fine uneven metal structure interacts with the sample and further a some sort of interaction between the fine uneven metal structure and Raman scattered light allowed a signal to be obtained from the back surface side which is comparable in intensity to that obtained from the front surface side.

In the present Example, a dried and fixed dye was used as the subject in the measuring sample, that is, the thickness of the subject was very thin so that the signals between the front surface side and back surface side of the dye on the gold film were almost identical in intensity. In the case where Raman spectroscopy is performed for a sample having a thickness in the order of one micrometer, such as a cell, however, it can be more advantageous to detect a signal near the interface between the gold film having a high enhancement effect and sample from the back surface side.

Such Raman signal detection from the back surface side of the substrate has been achieved for the first time by the measurement method and measurement apparatus using the optical field enhancement device having a transparent substrate body and a fine uneven structure. It is difficult for a measurement method and a measurement apparatus using a conventional optical field enhancement substrate configured such that an uneven structure is provided on an opaque substrate or an uneven structure made of an opaque material is provided on a transparent substrate to detect Raman scattered light from the back surface side of the substrate.

Heretofore, as it has not been considered that Raman light enhanced by an enhanced optical field created in the surface of an uneven metal structure can be detected from the back surface side of the substrate, the idea itself of fabricating the substrate and uneven structure with a transparent material has not existed in the first place and there has been no enhanced Raman device (optical field enhancement substrate) in which both of the substrate body and fine uneven structure are made of a transparent material.

Adoption of a configuration in which light is detected from the back surface side of the transparent substrate of the optical field enhancement substrate for not only the measurement of Raman spectroscopy but also for the measurement of fluorescence, second harmonics, Mie scattered light, and Rayleigh scattered light allows light generated from a subject on the metal film surface and enhanced to be detected without being blocked by the subject, whereby high signal intensity measurement may be realized.

What is claimed is:

1. A measurement method using an optical field enhancement device which includes a transparent substrate having a transparent fine uneven structure formed of boehmite on a surface and a metal film formed on a surface of the fine uneven structure on the surface of the substrate, the method comprising the steps:

placing a subject on the metal film of the optical field enhancement device;
projecting excitation light onto an area of the optical field enhancement device on which the subject is placed; and
detecting Raman scattered light generated from the subject by the projection of the excitation light from a back surface side of the transparent substrate.

2. The measurement method of claim 1, wherein the excitation light is projected from the back surface side of the transparent substrate.

3. A measurement apparatus, comprising:
an optical field enhancement device which includes a transparent substrate having a transparent fine uneven structure on a surface and a metal film formed on a surface of the fine uneven structure on the surface of the substrate, wherein a subject is placed on a front surface side of the device on which the metal film is formed;
an excitation light projection section for projecting excitation light onto an area of the optical field enhancement device on which the subject is placed; and
a light detection section disposed on a back surface side of the optical field enhancement device and configured to detect Raman scattered light generated from the subject by the projection of the excitation light from a back surface side of the transparent substrate,
the transparent substrate is formed of a transparent substrate body and a fine uneven structure layer formed of boehmite provided on a surface of the transparent substrate body.

4. The measurement apparatus of claim 3, wherein the excitation light projection section is disposed on the back surface side of the optical field enhancement device and configured to project the excitation light from the back surface side of the transparent substrate.

5. The measurement apparatus of claim 3, wherein the metal film of the optical field enhancement device has a film thickness of 10 to 100 nm.

6. The measurement apparatus of claim 3, wherein the apparatus comprises a transparent second fine uneven structure layer acting as an antireflection film on the back surface of the transparent substrate of the optical field enhancement device.

7. The measurement apparatus of claim 6, wherein the second fine uneven structure layer of the optical field enhancement device is made of boehmite.

8. The measurement apparatus of claim 3, wherein the optical field enhancement device comprises a liquid sample holding member for holding a liquid sample on the metal film of the transparent substrate.

9. The measurement apparatus of claim 8, wherein the liquid sample holding member of the optical field enhancement device has an inlet section and an outlet section for a liquid.

* * * * *